United States Patent [19]
Bleys et al.

[11] Patent Number: 6,034,149
[45] Date of Patent: Mar. 7, 2000

[54] HYDROPHILIC POLYURETHANE FOAMS

[75] Inventors: Gerhard Jozef Bleys, Heverlee; Dirk Gerber, Grimbergen; Henk Grymonprez, Zoutleeuw, all of Belgium

[73] Assignee: Imperial Chemical Industries PLC, London, United Kingdom

[21] Appl. No.: 09/112,879

[22] Filed: Jul. 9, 1998

[30] Foreign Application Priority Data

Jul. 9, 1997 [EP] European Pat. Off. ............... 97111608

[51] Int. Cl.⁷ ..................................................... C08G 18/14
[52] U.S. Cl. ........................... 521/155; 521/159; 521/174
[58] Field of Search ..................................... 521/174, 155, 521/159

[56] References Cited

U.S. PATENT DOCUMENTS

| 5,674,917 | 10/1997 | Wilson | 521/174 |
| 5,686,502 | 11/1997 | Murray et al. | 521/174 |
| 5,844,014 | 12/1998 | Malone | 521/155 |

FOREIGN PATENT DOCUMENTS

| 361 418 | 3/1990 | European Pat. Off. . |
| 470 697 | 2/1992 | European Pat. Off. . |
| 608 626 | 8/1994 | European Pat. Off. . |

*Primary Examiner*—John M. Cooney, Jr.
*Attorney, Agent, or Firm*—Pillsbury Madison & Sutro

[57] ABSTRACT

Hydrophilic flexible polyurethane foam which foam is in a compressed state above its glass transition temperature and at ambient pressure in the absence of force suitable to create the compressed state.

25 Claims, No Drawings

HYDROPHILIC POLYURETHANE FOAMS

The present invention is concerned with hydrophilic flexible polyurethane foams. Such foams are known; see e.g. WO94/29361 and WO 96/16099. Further it is known that such foams may be used to prepare absorbent articles like diapers, sponges, wound dressings and tampons. In general such absorbent articles are relatively voluminous; in particular diapers occupy a lot of space in shops and stores. It would be an advantage to reduce the volume of such absorbent articles without imparting the other properties.

In general flexible polyurethane foams show two major glass-rubber transitions. The commonly applied relatively high molecular weight polyether and polyester polyols in such foams are responsible for the first glass transition temperature ($Tg^s$). These polyether and polyester polyols are often referred to as soft segments. Above $Tg^s$ the foam displays its typical flexible properties until softening and/or melting of the isocyanate-derived urethane/urea clusters ("hard domains") takes place. This softening and/or melting temperature ($Tg^h$ and/or $Tm^h$) often coincides with the onset of thermal degradation of polymer segments. The $Tg^h$ and/or $Tm^h$ for flexible polyurethane foams is generally higher than 100° C., often even exceeding 200° C. At the $Tg^s$ a sharp decrease of the modulus of the flexible foam is observed. Between $Tg^s$ and $Tg^h/Tm^h$ the modulus remains fairly constant with increasing temperature and at $Tg^h/Tm^h$ again a substantial decrease of the modulus takes place. $Tg^s$ is measured by DSC (differential scanning calorimetry) with a Mettler, type TA4000 DSC equiped with a DSC 30 measuring cell at a heating rate of 30° C. per minute.

Polyurethane foams having shape memory properties are known; see EP-608626. Such foams remain deformed or compressed after they have been heated above their $Tg^s$, then compressed and finally cooled to a temperature below their $Tg^s$. Once they are heated to a temperature above their $Tg^s$ they will recover to their original shape and volume.

Surprisingly we have found that the foams like those of WO94/29361 and WO96/16099 may be compressed at elevated temperature by applying an external force onto the foam and subsequently cooled to ambient temperature. The cooling may be conducted before or after the force suitable to create the compressed state has been removed. When the external force is removed the foams stay in the compressed state. This is the more surprising since the glass transition temperature ($Tg^s$) of these foams is below ambient temperature. The foams of the present invention remain in the compressed state, even above their $Tg^s$.

The wicking-, absorption- and retention properties of these compressed foams are not seriously negatively influenced by the compression.

Therefore the present invention is concerned with a hydrophilic flexible polyurethane foam which is in a compressed state at a temperature above its glass transition temperature ($Tg^s$) and at ambient pressure in the absence of a force suitable to create the compressed state.

The hydrophilic flexible polyurethane foams according to the present invention preferably are made by reacting a prepolymer having an NCO value of 3–15% by weight, which is the reaction product obtained by reacting an excessive amount of a polyisocyanate with a polyether-polyol or a mixture of such polyols, said polyol or mixture having an average nominal hydroxyl functionality of from 2 to 6 and preferably of from 2 to 4, an average hydroxyl equivalent weight of from 500 to 5000 and preferably from 1000 to 5000 and an oxyethylene content of at least 50% by weight, with water, the amount of water being 15–500 parts by weight per 100 parts by weight of prepolymer. A more preferred embodiment to make these foams is by reacting a prepolymer, having an NCO value of 3–10% by weight which is the reaction product obtained by reacting an excessive amount of a polyisocyanate containing at least 65, preferably at least 90, and more preferably at least 95% by weight of 4,4'-diphenyl methane diisocyanate or a variant thereof with a polyether polyol or a mixture of said polyols, said polyol or mixture having an average nominal hydroxyl functionality of from 2.5 to 3.5, an average hydroxyl equivalent weight of from 1000 to 3000, and an oxyethylene content of from 50 to 85% by weight, with water, the amount of water being 30–300 parts by weight per 100 parts by weight of prepolymer. Preferably at the start of the reaction the temperature of the prepolymer is 10–50° C., preferably 15–30° C. and most preferably room temperature and the temperature of the water is 10–50° C., preferably 20–45° C. higher than the temperature of the prepolymer. The temperature of the water is 25–90° C., preferably 40–70° C., most preferably 55–65° C.

For the sake of convenience the word average in the present application is not further specified but refers to number average unless explicitly used otherwise.

Polyisocyanates used for preparing the prepolymer may be selected from aliphatic, cycloaliphatic and araliphatic polyisocyanates, especially diisocyanates, like hexamethylene diisocyanate, isophorone diisocyanate, cyclohexane-1,4-diisocyanate, 4,4'-dicyclohexylmethane diisocyanate and m- and p-tetramethylxylylene diisocyanate, and in particular aromatic polyisocyanates like toluene diisocyanates (TDI), phenylene diisocyanates and most preferably methylene diphenylene diisocyanates (MDI) and its homologues having an isocyanate functionality of more than two, like crude MDI and polymeric MDI.

Preferred polyisocyanates are methylene diphenylene diisocyanates selected from pure 4,4'-MDI, isomeric mixtures of 4,4'-MDI and 2,4'-MDI and less than 10% by weight of 2,2'-MDI, and modified variants thereof containing carbodiimide, uretonimine, isocyanurate, urethane, allophanate, urea or biuret groups, like uretonimine and/or carbodiimide modified MDI having an NCO content of at least 25% by weight and urethane modified MDI obtained by reacting excess MDI and a low molecular weight polyol (MW up to 1000) and having an NCO content of at least 25% by weight.

Mixtures of the isocyanates mentioned above may be used if desired. The polyisocyanate may contain dispersed urea particles and/or urethane particles prepared in a conventional way, e.g. by adding a minor amount of an isophorone diamine to the polyisocyanate.

The most preferred polyisocyanate used in preparing the prepolymer is a polyisocyanate containing at least 65%, preferably at least 90% and more preferably at least 95% by weight of 4,4'-diphenyl methane diisocyanate or a variant thereof. It may consist essentially of pure 4,4'-diphenyl methane diisocyanate or mixtures of that diisocyanate with one or more other organic polyisocyanates, especially other diphenyl methane diisocyanate isomers, for example the 2,4'-isomer optionally in conjunction with the 2,2'-isomer. The most preferred polyisocyanate may also be an MDI variant derived from a polyisocyanate composition containing at least 65% by weight of 4,4'-diphenylmethane diisocyanate. MDI variants are well known in the art and, for use in accordance with the invention, particularly include liquid products obtained by introducing uretonimine and/or carbodiimide groups into said polyisocyanates, such a carbodiimide and/or uretonimine modified polyisocyanate preferably having an NCO value of at least 25% by weight, and/or by reacting such a polyisocyanate with one or more polyols having a hydroxyl functionality of 2–6 and a molecular weight of 62–1000 so as to obtain a modified polyisocyanate, preferably having an NCO value of at least 25% by weight.

The polyether polyol or mixture of polyether polyols used in preparing the prepolymer preferably has an average nominal hydroxyl functionality of 2–4 and most preferably of 2.5–3.5 and an average hydroxyl equivalent weight of 1000–3000 and an oxyethylene content of from 50–85% by weight.

Polyether polyols include products obtained by the polymerisation of ethylene oxide optionally together with another cyclic oxide like tetrahydrofuran and—preferably—propylene oxide in the presence, where necessary, of polyfunctional initiators. Suitable initiator compounds contain a plurality of active hydrogen atoms and include water, butanediol, ethylene glycol, propylene glycol, diethylene glycol, triethylene glycol, dipropylene glycol, ethanolamine, diethanolamine, triethanolamine, toluene diamine, diethyl toluene diamine, phenyl diamine, diphenylmethane diamine, ethylene diamine, cyclohexane diamine, cyclohexane dimethanol, resorcinol, bisphenol A, glycerol, trimethylolpropane, 1,2,6-hexanetriol, pentaerythritol and sorbitol. Mixtures of initiators may be used.

If another cyclic oxide is used the polyol may be obtained by the simultaneous or sequential addition of ethylene oxide and the other cyclic oxide as fully described in the prior art.

In order to obtain the preferred polyol having an average nominal hydroxyl functionality of 2.5 to 3.5 a polyol having a nominal hydroxyl functionality of 3 may be used or a mixture of polyols having an average nominal hydroxyl functionality of 2–6 provided the mixture is in the above 2.5–3.5 functionality range.

In general polyol mixtures may be used provided they have the required functionality, equivalent weight and oxyethylene content as described above.

The term "average nominal hydroxyl functionality" is used herein to indicate the average functionality (number of hydroxyl groups per molecule) of the polyol composition on the assumption that the average functionality of the polyoxyalkylene polyols present therein is identical with the average functionality (number of active hydrogen atoms per molecule) of the initiator(s) used in their preparation although in practice it will often be somewhat less because of some terminal unsaturation.

If desired, the polyether polyol or the mixture of polyols may contain dispersed polymer particles. Such polymer-modified polyols have been fully described in the prior art and include products obtained by the in situ polymerisation of one or more vinyl monomers, for example acrylonitrile and styrene, in polyoxyalkylene polyols or by the in situ reaction between a polyisocyanate and an amino- or hydroxy-functional compound, for example triethanolamine, in the polyoxyalkylene polyol.

The prepolymer is prepared conventionally by reacting the polyisocyanate and the polyol at relative amounts so as to obtain an NCO value of 3–15% by weight, preferably of 3–10% by weight at a temperature preferably between 40 and 90° C. The prepolymers so prepared are liquid at ambient conditions. To the prepolymer so prepared low amounts (up to 30% by weight) of further polyisocyanate and in particular MDI may be added if desired. In order to improve the stability of the prepolymer a small amount of an organic acid or Lewis acid may be added.

The prepolymer preferably has a viscosity of at most 10.000 mPa.s at 25° C.

In preparing the prepolymer it preferably should be avoided that the isocyanate functionality of the polyisocyanate and the average nominal hydroxyl functionality of the polyol or mixture of polyols are both 2.0. If one of these functionalities is 2.0 the other one preferably is at least 2.2.

The prepolymer is reacted with water, the amount of water being 15–500, preferably 30–300, most preferably 40–250 parts by weight per 100 parts by weight of prepolymer.

The foam-forming reaction mixture may contain one or more of the additives used in preparing flexible foams. Such additives include catalysts, for example tertiary amines and tin compounds, surface-active agents and foam stabilisers, for example siloxane-oxyalkylene copolymers and polyoxyethylene/polyoxypropylene copolymers and polyoxyethylene polymers, chain extenders, for example low molecular weight diols or diamines, cross-linking agents, for example triethanolamine, glycerol and trimethylolpropane, flame retardants, organic and inorganic fillers, pigments, agents for suppressing the so-called boiling-foam effect like polydimethylsiloxanes, internal mould release agents, anticeptics, biocides and medicaments. However, valuable flexible foams may be obtained without any of these additives. Preferably no additives are applied except up to 10 parts and preferably up to 5 parts by weight of the aforementioned polyoxyethylene/polyoxypropylene copolymers and polyoxyethylene polymers per 100 parts by weight of prepolymer. If used, such additives preferably are pre-mixed with the water.

As to the use of these (co)polymers it was found that foams, which exhibit very good wicking properties and are able to absorb and retain water in an amount of several times the weight of the foam and/or which have reticulated cells, could be made when the prepolymer and the water are reacted in the presence of 0.01–10 parts by weight, per 100 parts by weight of prepolymer, of a polyol having an average molecular weight of 500–10000 and an average nominal hydroxyl functionality of 2–6, this polyol being a polyoxyethylene polymer or a polyoxyethylene polyoxypropylene block copolymer having an oxyethylene content of at least 30% by weight. This polyol preferably is used in an amount of 0.05–3 parts by weight per 100 parts by weight of prepolymer. These polyols are known in the art and commercially available. Examples are Synperonic™ PE L44, L64, F68, P75, P84, P85 and F87, all available from Imperial Chemical Industries PLC.

When these polyols are used the wicking properties are especially obtained when polyols are used having an oxyethylene content of 35–70 and more in particular 40–70% by weight; preferably the average nominal hydroxyl functionality of such polyols is 2. When these polyols are used the reticulated properties are especially obtained when polyols are used having an oxyethylene content of 70–100 and optimally 100% by weight; it is preferred to use at least 40 parts by weight of water per 100 parts by weight of prepolymer for preparing such reticulated foams.

Before the prepolymer and the water are reacted in the presence of this polyol, the water and this polyol preferably are premixed.

Further the process to prepare the foams may be conducted in the presence of superabsorbent polymers or ingredients to prepare such superabsorbent polymers or the foams formed may be impregnated with such superabsorbent polymers.

Superabsorbent polymers (SAP) are widely known as such. SAP or water-absorbent polymers or hydrogels are water-insoluble hydrophilic polymers, able to swell and absorb amounts of water, saline solutions, physiological fluids or body fluids as high as 10–100 times their own weight. They consist of polyelectrolytes or other highly hydrophilic polymeric matrices, usually bearing crosslinking sites along the macromolecular chains in order to avoid dissolution. They may be natural SAPs, like guar gum, other natural gums and starches and, preferably, synthetic SAPs which include polymers based on acrylic or methacrylic acids, esters, nitrites, amides and salts thereof, polysaccharides, maleic anhydride polymers, poly(vinyl) alcohol, poly(N-vinyl-pyrrolidone) and diallyl dialkyl quaternary ammonium salts. For an overview of SAP we refer to a review article "Water-Absorbent Polymers: A Patent Survey" of Riccardo PO in J. M. S—Rev. Macromol. Chem. Phys., C34 (4), 607–662(1994). The superabsorbent polymers disclosed in this article may be used in the present invention.

SAPs based on acrylic or methacrylic monomers are polymers made by free radical polymerization of acrylic or methacrylic acids, esters, nitrites, amides and/or salts thereof optionally together with other unsaturated monomers like maleic, fumaric or itaconic derivatives, vinyl substituted sulfonic or ammonium salts, olefinic and styrenic monomers, hydroalkyl or alkyl acrylates and methacrylates, unsaturated sulfonic acid salts, acrylamidoalkyl sulfonic salts, vinyl sulfonate, styrene sulfonate, vinylbenzyl sulfonate, N,N'-methylenebisacrylamide, dialkylaminoalkyl acrylate and methacrylate, carbonyl containing heterocyclic N-vinyl monomers like N-vinyl-2-pyrrolidone, N-vinyl-2-caprolactam and N-vinyl-2-morpholinone. The polymers may be prepared by processes known in the art using if desired initiators, cross-linkers and surfactants as known in the art; see e.g. PO, pages 610–632. Cross-linking may be carried out by free radical copolymerization of small amounts of polyvinylic comonomers or by reaction of the pendent carboxylate or carboxylic groups of the polymer with a polyepoxide, a haloepoxide and/or a polyol.

Polysaccharide based superabsorbent polymers may be selected from e.g. starch graft copolymers and modified cellulose polymers. Such SAPs are obtained by grafting an unsaturated monomer like acrylonitrile, acrylic acid or acrylic amide onto a polysaccharide like starch or cellulose, optionally followed by saponification. Such polysaccharide based superabsorbent polymers are known in the art and may be prepared by processes known in the art; see PO, pages 632–638.

SAPs based on maleic anhydride polymers are made by reacting maleic anhydride and hydrophobic comonomers like an olefin or vinylether by processes known in the art; see PO, pages 638–642.

Further SAPs which may be used are polymers prepared by polymerizingdiallyl dialkyl quaternary ammonium salts in the presence of a polyfunctional divinyl compound and/or a crosslinker like triallyl methylammonium chloride; polyalkylene oxides like polyethyleneoxide which have been cross-linked with e.g. formaldehyde and glutaraldehyde in the presence of sulphuric acid; poly(N-vinyl pyrrolidone) and poly(N-methyl, N-vinyl acetamide) which have been cross-linked by means of e.g. divinylbenzene, diacrylates or diethylene glycol divinylether. Such SAPs and the way they are made are known in the art; see PO, pages 642–647.

Preferred SAPs are selected from super absorbent polymers based on acrylic or methacrylic acids, esters, nitriles, amides and/or salts thereof; polysaccharide based superabsorbent polymers and superabsorbent polymers based on maleic anhydride.

There are three ways to incorporate SAP in the polyurethane foam:

1. The ingredients for making the SAP and the ingredients for making the polyurethane foam are combined and the SAP and the polyurethane foam are allowed to be formed at the same time; see e.g. U.S. Pat. No. 4,731, 391, and EP-163150. The result is an interpenetrating network.
2. The SAP is incorporated in the polyurethane foam by impregnation using a liquid as a carrier for the SAP; see EP-4 1934.
3. The SAP particles are mixed with the ingredients used for making the flexible foam. This option is preferred The amount of superabsorbent polymer used in general will be 1 to 100 parts by weight (pbw) per 100 parts by weight of prepolymer and more preferably 5 to 80 pbw and most preferably 10 to 70 pbw. Since most of the water used is not consumed in the blowing reaction and since hardly other ingredients are used the weight of the foam is only slightly different from the weight of the prepolymer used. Therefore the amount of SAP per 100 pbw of foam is 1–100, preferably 5–80 and most preferably 10–70 pbw.

The SAPs may be selected from those described in the article of PO as discussed before. More in particular they may be selected from cross-linked polyacrylates and polyacrylamides and the salts thereof. Such SAPs are commercially available; e.g. SANWET™ IM3900G, IM 3746/1 and E394-95 from Hoechst/Cassella. Further SAPs may be selected from starch or cellulose grafted SAPs, using e.g. acrylonitrile, acrylic acid or acrylic amide as the unsaturated monomer. Such SAPs are also commercially available; e.g. SANWET IM7000 from Hoechst/Cassella.

Different SAPs may be used in combination. The SAPs may be mixed with the prepolymer and the water at the moment this prepolymer and water are mixed or the SAPs are premixed with the prepolymer. Preferably the SAPs are not premixed with the water. The mixing may be conducted by means of hand-mixing or normal machine mixing or under high shear mixing conditions.

The foams have very desirable properties: they exhibit limited shrinkage, have open-cells, are stable, do not show scorching and have very good water-absorbtion and water-retention characteristics, very good wicking properties and mechanical properties like tear strength (dry and wet) and elongation and have a desirable colour (white).

The purity and simplicity of the chemicals used for making the prepolymers ensures that flexible foams made thereof have a minimum of leachable substances which make these foams especially useful in areas where contact with a human body is required like in medical and hygienic applications.

The foams may be produced in the form of slabstock, mouldings and the like and may be used for vibration damping, diapers, sponges, wound dressings, tampons, cosmetic pads, drug release products, plant growth media, absorbent in food trays and the like.

The foams as described above then are compressed, preferably after they have been dried. The degree of compression depends on the thickness reduction desired. Preferably the thickness reduction is such that the thickness of the compressed foam in the absence of a force suitable to create the compressed state is at most 90%, more preferably at most 70% and most preferably at most 60% of the thickness of the foam before it was compressed. Since the foam might recover slightly after the force, applied to create the compressed state, has been removed the compression is conducted in such a way that the thickness of the foam when the compression is applied is 0–50 and preferably 0–30% lower than the above figures for the thickness of the foam after the force suitable for creating the compressed state has been removed. The compression may be conducted in one or more of the dimensional directions of the foam. Although in general not necessary, the compression may be repeated after decompression. The compression may be conducted by applying any force suitable like compression of the foam between two or more flat plates, two or more rollers or two conveyor belts.

The compression is conducted for a period of 1–60 minutes, preferably 1–50 minutes and most preferably 1–30 minutes during which period the foam is kept at a temperature of 80–160° C., preferably 90–150° C. and most preferably 100–140° C. If desired the foam may be preheated before the compression at the above indicated temperature.

After compression has been conducted for the indicated period the force is removed and the foam is cooled to ambient temperature, which in the context of the present invention is 5–40° C. The foams according to the present invention have a glass transition temperature ($Tg^s$) below 0° C. The hydrophilic flexible foams which remain in the compressed state after the force suitable to create the compressed state has been removed and after the foam has been cooled to ambient temperature which temperature is above the glass transition temperature ($Tg^s$) are foams according to the present invention irrespective of their state of compression outside the ambient temperature range and irrespective of the fact whether or not the force is actually removed.

In the context of the present application a foam is regarded as hydrophilic if it can absorb at least 1000 g of water/dm$^3$ of dry foam; dry meaning that the foam has been kept at 50° C. for 24 hours in air having a relative humidity of at most 10%.

Further the invention is concerned with articles, in particular sanitary articles, like diapers, sponges, wound dressings and tampons comprising such compressed foams. Preferably the foam is based on diphenyl methane diisocyanate as the polyisocyanate. The application is illustrated by the following examples.

EXAMPLE 1

Polyol 1 is a polyether (triol-initiated) having random oxyethylene and oxypropylene residues with about 75% oxyethylene content and a molecular weight of about 4000.

100 parts by weight of prepolymer was prepared by reacting 70 parts by weight (pbw) of polyol 1 and 30 parts by weight of 4,4'-MDI. From this prepolymer a flexible foam was prepared by mixing it with 70 pbw of water containing 1% by weight of Synperonic L64 (an EO/PO surfactant from ICI-Synperonic is a trademark of ICI) and allowed to react in an open container. The prepolymer had an NCO value of 7.85% by weight and a viscosity of 6000 mPa.s at 25° C. The temperature of the prepolymer was kept at room temperature (22° C.) and the temperature of the water was 45° C. prior to reaction. The foam obtained was cooled to ambient temperature and cut in samples having dimensions 50 mm×50 mm×about 18–21 mm (Foam 1).

EXAMPLE 2

100 pbw of the prepolymer prepared in example 1 was mixed with 1.8 pbw of water and 0.1 pbw of Niax A1 catalyst and allowed to react in an open container. The temperature of both ingredients before the reaction was at ambient temperature. The foam obtained was cooled at ambient temperature and cut in samples as above (Foam 2)

EXAMPLE 3

All foam samples were dried at 50° C. for 24 hours in air having a relative humidity of at most 10%. Then they were compressed between flat plates which were preheated at a certain temperature, which was maintained during compression, and for a certain period of time (experiment 1–7). In experiments 8–11 the foams were compressed between flat plates in an oven and in air having a relative humidity of at most 10% for a certain period of time, during this period the certain temperature was maintained. The compression was conducted in such a way that the initial thickness of the samples of about 18–21 mm was reduced to a certain thickness. After the compression time the plates are removed and the sample is allowed to cool to ambient temperature (22° C.). The thickness of the samples was measured a certain period after the compression was stopped. The varied parameters and the results are in the Table below. For experiments 1–3 absorption and for experiments 1–3 and 8–9 swell were calculated as follows:

swell:

$$\frac{T_a - T_b}{T_b} \times 100\%, \text{ wherein } T_b \text{ and } T_a \text{ are the thickness of the foam before and after absorption, respectively}$$

absorption: the maximal absorption was determined by completely immersing the foam in water for 15 seconds, followed by taking the foam out of water and by determining the weight difference of the foam after and before immersing.

Then the percentage absorption is calculated as follows:

$$\% \text{ absorption} = \frac{\text{weight (wet sample)} - \text{weight (dry sample)}}{\text{weight (dry sample)}} \times 100$$

The corrected absorption (g of absorbed water/l of foam) is calculated as:

Gram absorption/litre of foam =

$$\frac{\text{absorption } (\%) \times \text{density of the dry sample } (g/dm^3)}{100}$$

The density was determined by method ISO 845.

| Experiment | Foam | Exact Thickness of sample before compression | Compression temperature, °C. | Compression time, min | Compression of sample to a thickness of (mm) | Thickness after removing compression (mm) after | | | absorption g/l foam | swell, % |
|---|---|---|---|---|---|---|---|---|---|---|
| | | | | | | 1 min | 1 day | 2 days | | |
| 1  | 1 | 18.5 | 0   | 0  | —  | —    | —    | —   | 445  | 18 |
| 2  | 1 | 21   | 110 | 20 | 10 | —    | —    | 11  | 2830 | 10 |
| 3  | 1 | 21   | 110 | 25 | 10 | —    | —    | 10  | 2830 | 0  |
| 4  | 1 | 18.5 | 130 | 6  | 7  | —    | —    | 7.8 | —    | —  |
| 5  | 1 | 18.5 | 130 | 10 | 7  | —    | —    | 7   | —    | —  |
| 6  | 1 | 18.5 | 150 | 6  | 7  | —    | —    | 6.3 | —    | —  |
| 7  | 1 | 18.5 | 150 | 4  | 7  | —    | —    | 68  | —    | —  |
| 8  | 1 | 18.2 | 110 | 20 | 8  | 14.2 | 14.4 | —   | —    | 18 |
| 9  | 1 | 17.5 | 110 | 25 | 8  | 10.1 | 10.0 | —   | —    | 19 |
| 10 | 2 | 18.8 | 110 | 20 | 8  | 16.7 | 18.2 | —   | —    | —  |
| 11 | 2 | 18.8 | 110 | 25 | 8  | 17.7 | 18.2 | —   | —    | —  |

We claim:

1. Hydrophilic flexible polyurethane foam which foam is in a compressed state at a temperature above its glass transition temperature (Tg$^s$) and at ambient pressure in the absence of a force suitable to create the compressed state.

2. Foam according to claim 1 wherein the glass transition temperature is below 0° C. and the foam is in a compressed state at a temperature between 5 and 40° C.

3. Foam according to claim 1 wherein the thickness of the foam is at most 90% of the thickness before compression.

4. Foam according to claim 1 wherein the thickness of the foam is at most 70% of the thickness before compression.

5. Foam according to claim 1 wherein the thickness of the foam is at most 60% of the thickness before compression.

6. Foam according to claim 1 wherein the foam has been made by reacting a prepolymer having an NCO value of 3–15% by weight, which is the reaction product obtained by reacting an excessive amount of a polyisocyanate with a polyether polyol or a mixture of such polyols, said polyol or mixture having an average nominal hydroxyl functionality of from 2 to 6, an average hydroxyl equivalent weight of from 500 to 5000 and an oxyethylene content of at least 50% by weight, with water, the amount of water being 15–500 parts by weight per 100 parts by weight of prepolymer, at the start of the reaction the temperature of the prepolymer being 10–50° C. and the temperature of the water being 10–50° C. higher than the temperature of the prepolymer.

7. Foam according to claim 6 wherein at the start of the reaction the temperature of the water is 25–90° C.

8. Foam according to claim 6 wherein the temperature of the prepolymer is 15–30° C., the temperature of the water is 40–70° C. and the temperature of the water is 20–45° C. higher than the temperature of the prepolymer.

9. Foam according to claim 6 wherein the prepolymer is a prepolymer having an NCO value of 3–10% by weight which is the reaction product obtained by reacting an excessive amount of a polyisocyanate containing at least 65% by weight of 4,4'-diphenylmethane diisocyanate or a variant thereof and the polyol or mixture of polyols has an average nominal hydroxyl functionality of from 2.5 to 3.5, an average hydroxyl equivalent weight of from 1000 to 3000, and an oxyethylene content of from 50 to 85% by weight and the amount of water is 30–300 parts by weight per 100 parts by weight of prepolymer.

10. Foam according to claim 6 wherein the reaction between the prepolymer and the water is conducted in the presence of 0.01–10 parts by weight, per 100 parts by weight of prepolymer, of a polyol (2) having an average molecular weight of 500–10000 and an average nominal hydroxyl functionality of 2–6, this polyol being a polyoxyethylene polymer or a polyoxyethylene polyoxypropylene block copolymer having an oxyethylene content of at least 30% by weight.

11. Foam according to claim 10 wherein polyol (2) has an average nominal hydroxyl functionality of 2 and an oxyethylene content of 35–70% by weight.

12. Foam according to claim 10 wherein polyol (2) has an oxyethylene content of at least 70% by weight and the amount of water used is at least 40 parts by weight per 100 parts by weight of prepolymer.

13. Foam according to claim 1 wherein the foam comprises a superabsorbent polymer.

14. Foam according to claim 13 wherein the superabsorbent polymer is selected from superabsorbent polymers based on acrylic or methacrylic acids, esters, nitrites, amides and/or salts thereof; polysaccharide based superabsorbent polymers and superabsorbent polymers based on maleic anhydride.

15. Foam according to claim 13 wherein the amount of super absorbent polymer is 10–70 parts by weight per 100 parts by weight of foam.

16. Foam according to claim 1 which is catalyst-free and based on diphenylmethane diisocyanate as the polyisocyanate.

17. Process for making a foam according to claim 1 by applying a force to the foam suitable to compress the foam at a temperature of 80–160° C. for a period of 1–60 minutes, removing the force and allowing the foam to cool to ambient temperature.

18. Process according to claim 17 wherein the temperature is 90–150° C. and the period is 1–50 minutes.

19. Process according to claim 17 wherein the temperature is 100–140° C. and the period is 1–30 minutes.

20. Process according the claim 17 wherein the force applied is suitable to reduce the thickness of the foam to a thickness which is at most 90% of the thickness before compression.

21. Process according to claim 20 wherein this thickness is at most 70%.

22. Process according to claim 20 wherein this thickness is at most 60%.

23. Article comprising a foam according to claim 1.

24. Article according to claim 23 wherein the article is a sanitary article.

25. Article according to claim 23 wherein the article is a diaper.

* * * * *